(12) United States Patent
Woerlein et al.

(10) Patent No.: US 9,974,615 B2
(45) Date of Patent: May 22, 2018

(54) DETERMINING A POSITION OF A MEDICAL DEVICE TO BE LOCALIZED

(75) Inventors: Swen Woerlein, Munich (DE); Johannes Manus, Munich (DE)

(73) Assignee: Brainlab AG, Munich (DE)

( * ) Notice: Subject to any disclaimer, the term of this patent is extended or adjusted under 35 U.S.C. 154(b) by 995 days.

(21) Appl. No.: 14/346,883

(22) PCT Filed: Sep. 28, 2011

(86) PCT No.: PCT/EP2011/066802
§ 371 (c)(1),
(2), (4) Date: Mar. 24, 2014

(87) PCT Pub. No.: WO2013/044944
PCT Pub. Date: Apr. 4, 2013

(65) Prior Publication Data
US 2014/0316257 A1    Oct. 23, 2014

(51) Int. Cl.
*A61B 19/00* (2006.01)
*A61B 5/06* (2006.01)
*A61B 34/20* (2016.01)

(52) U.S. Cl.
CPC .......... *A61B 19/5244* (2013.01); *A61B 5/061* (2013.01); *A61B 34/20* (2016.02);
(Continued)

(58) Field of Classification Search
CPC ........ A61B 19/5244; A61B 2034/2055; A61B 2034/2068; A61B 2034/2074; A61B 34/20; A61B 5/061
See application file for complete search history.

(56) References Cited

U.S. PATENT DOCUMENTS 6,175,756 B1 * 1/2001 Ferre ................... A61B 34/20
                                                        600/424
6,402,762 B2    6/2002 Hunter et al.
(Continued)

FOREIGN PATENT DOCUMENTS

DE    197 51 761    6/2006
EP    0 672 389     8/1998
(Continued)

OTHER PUBLICATIONS

International Search Report and Written Opinion for International Application No. PCT/EP2011/066802 dated Jun. 27, 2012.
(Continued)

*Primary Examiner* — Ruth S Smith
(74) *Attorney, Agent, or Firm* — Tucker Ellis LLP

(57) ABSTRACT

A method of determining the position of a medical device to be localized, comprising:
  a) acquiring main position data comprising reference structure position information which describes the position of a reference structure in a global coordinate system, the main position data having been gathered by a main detection device;
  b) acquiring supplement position data comprising relative position information which describes the position of the medical device relative to the position of the reference structure in a reference coordinate system, the supplement position data having been gathered by a supplement detection device;
  c) determining, based on the relative position information and the reference structure position information, medical device position data comprising medical device position information which describes the position of the medical device in the global coordinate system.

14 Claims, 2 Drawing Sheets

Figure 1:
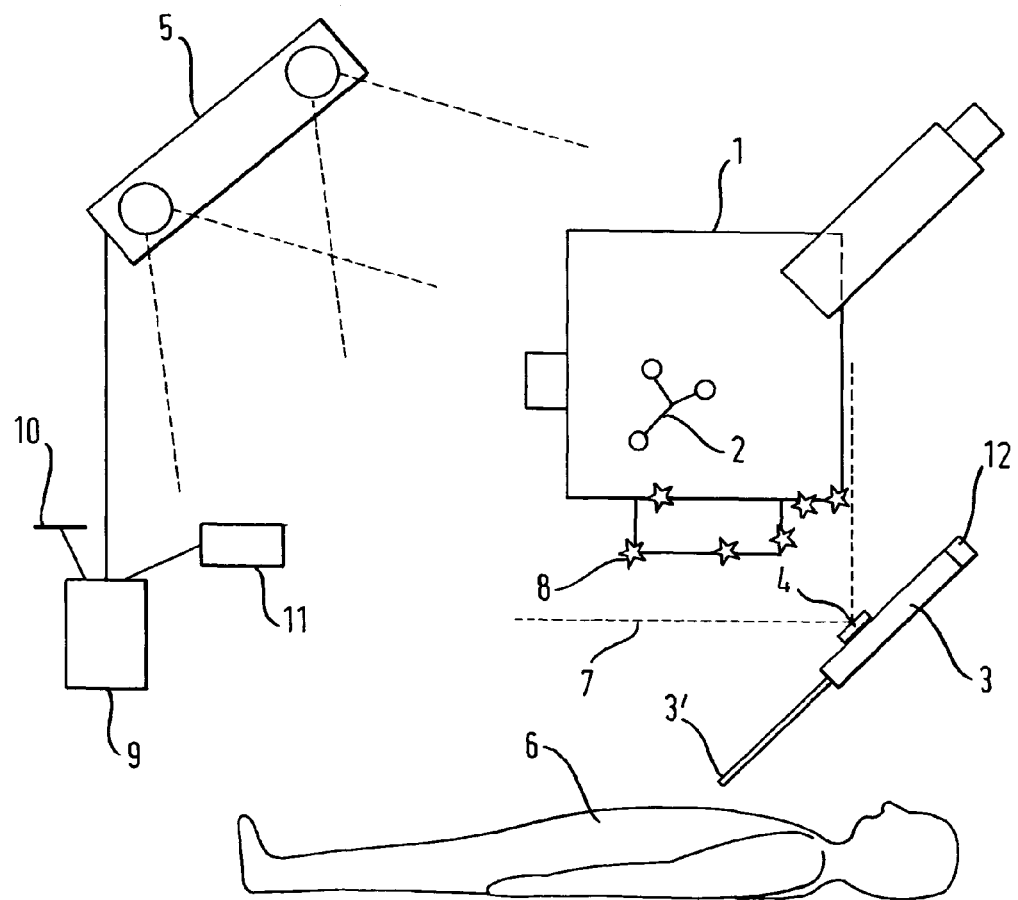

(52) U.S. Cl.
CPC ............... *A61B 2034/2055* (2016.02); *A61B 2034/2068* (2016.02); *A61B 2034/2074* (2016.02)

(56) References Cited

U.S. PATENT DOCUMENTS

| | | | |
|---|---|---|---|
| 2006/0173356 A1* | 8/2006 | Feilkas | A61B 5/06 600/476 |
| 2010/0228117 A1 | 9/2010 | Hartmann | |
| 2011/0015518 A1 | 1/2011 | Schmidt et al. | |

FOREIGN PATENT DOCUMENTS

| | | |
|---|---|---|
| EP | 1 096 268 | 12/2006 |
| EP | 1 857 070 | 11/2007 |
| EP | 2 153 794 | 2/2010 |
| WO | 2006095027 A1 | 9/2006 |
| WO | 2006131373 | 12/2006 |
| WO | 2008008044 | 1/2008 |
| WO | 2008030275 | 3/2008 |
| WO | 2011113483 | 9/2011 |

OTHER PUBLICATIONS

European Patent Office, European Search Report for related European divisional application No. EP17175467.4, pp. 1-5, date of completion Sep. 14, 2017, Munich, Germany.

\* cited by examiner

DETERMINING A POSITION OF A MEDICAL DEVICE TO BE LOCALIZED

RELATED APPLICATION DATA

This application is a national phase application of International Application No. PCT/EP2011/066802 filed Sep. 28, 2011 and published in the English language.

The present invention is directed to a method and system for acquiring the position of a medical device to be localized as defined by the independent claims.

Within the framework of this invention, the term of localizing a medical device encompasses acquiring the position of the medical device in a specific coordinate system, in particular a global coordinate system in which the spatial environment in which the medical device is used rests relative to for example a patient's body or a room in which the patient's body is present but preferably not relative to the medical device. In particular, localizing a medical device encompasses determining a position of the medical device relative to in particular a patient's body or an anatomical body part (i.e. an anatomical region). More particularly, the term of localizing also encompasses the term of tracking.

Medical devices are commonly localized by tracking which encompasses the use of electromagnetic radiation for example by determining a response signal which is received from a retroreflective marker attached to the medical device or which is absorbed by a marker device which is opaque for X-rays. If now an obstacle is placed in the line of sight between a transmitter and/or receiver of the electromagnetic radiation and the responding device such as the marker device, problems will occur in determining the position of the medical device if the obstacle is not transparent for the respectively used electromagnetic frequencies. Prior art approaches to this problem include parallel (i.e. simultaneous) employment of different modalities of position determination (i.e. tracking modalities) which support localizing the medical device even in case of line of sight problems. However, the tracking modalities applied in parallel again rely on the mentioned techniques and potentially also suffer from the line of sight problem.

A problem to be solved by the present invention therefore is to provide a method and corresponding system which support localizing a medical device even in case of a line of sight problem in an efficient manner.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The medical device which is to be localized within the framework of the invention in particular is an instrument which is in particular intended for use on a patient's body (such as, for example, a catheter, a scalpel or a pointer) or any other in particular solid physical structure which is intended for use in a medical procedure (such as, for example, devices used in an operating theatre such as a patient bed, a lamp, or the computer of a navigation system).

The reference structure is in particular also a (in particular solid) physical structure which can be intended for use in the medical procedure (such as a bed, a lamp, a microscope, CT-arc, computer etc.) and is in particular constituted so that is position is detectable by the main detection device and the supplement detection device. The reference structure comprises in particular a marker device (like a set of one or more markers, in particular a reference star). Also an anatomical structure or a marker device attached to an anatomical structure can (or cannot) optionally serve as a reference structure.

A pointer is a rod which comprises one or more—advantageously, two—markers fastened to it and can be used to measure off individual co-ordinates, in particular spatial co-ordinates (i.e. three-dimensional co-ordinates), on a part of the body within the framework of a morphing method, wherein a user guides the pointer (in particular, a part of the pointer which has a defined and advantageously fixed location with respect to the at least one marker attached to the pointer) to the position corresponding to the co-ordinates, such that the position of the pointer can be determined by using a navigation system to detect the marker on the pointer. The relative location between the markers of the pointer and the part of the pointer used to measure off co-ordinates (in particular, the tip of the pointer) is in particular known. The navigation system then enables the location (of the three-dimensional coordinates) to be assigned to a predetermined body structure, wherein the assignment can be made automatically or by user intervention.

It is the function of a marker to be detected by a marker detection device (for example, a camera or an ultrasound receiver), such that its spatial position (i.e. its spatial location and/or alignment) can be ascertained. The detection device is in particular part of a navigation system. The markers can be active markers. An active marker can for example emit electromagnetic radiation and/or waves, wherein said radiation can be in the infrared, visible and/or ultraviolet spectral range. The marker can also however be passive, i.e. can for example reflect electromagnetic radiation in the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can also, however, exhibit a cornered—for example, cubic—shape.

A "reference star" refers to a device with a number of markers, advantageously three markers, attached to it, wherein the markers are (in particular detachably) attached to the reference star such that they are stationary, thus providing a known (and advantageously fixed) position of the markers relative to each other. The position of the markers relative to each other can be individually different for each reference star used within the framework of a surgical navigation method, in order to enable the corresponding reference star to be identified by a surgical navigation system on the basis of the position of the markers relative to each other. It is therefore also then possible for the objects (for example, instruments and/or parts of a body) to which the reference star is attached to be identified and/or differentiated. In a surgical navigation method, the reference star serves to attach a plurality of markers to an object (for example, a bone or a medical instrument) in order to be able to detect the position of the object (i.e. its spatial location and/or alignment). Such a reference star in particular comprises a way of being attached to the object (for example, a clamp and/or a thread) and/or a holding element which ensures a distance between the markers and the object (in particular in order to assist the visibility of the markers to a marker detection device) and/or marker holders which are mechanically connected to the holding element and which the markers can be attached to.

A marker device can for example be a reference star or a pointer or one or more (individual) markers in a predetermined spatial relationship. A marker device comprises one, two, three or more markers in a predetermined spatial relationship. This predetermined spatial relationship is in particular known to a navigation system and for example stored in a computer of the navigation system.

A navigation system, in particular a navigation system for computer-assisted surgery, preferably comprises a computer for processing the data provided in accordance with the data processing method as described in any one of the preceding embodiments. The navigation system preferably comprises a detection device for detecting the position of markers on the basis of the detection signals received and based on the aforementioned functional principles of marker technology. These detection signals are acquired as digital data by the computer. The navigation system also preferably comprises a user interface for receiving the calculation results from the computer (for example, numeric and/or graphical information about a marker position). The user interface provides the received data to the user as information. Examples of a user interface include a monitor or a loudspeaker. The user interface can use any kind of indication signal (for example a visual signal, an audio signal and/or a vibration signal).

A pointer is preferably used to identify specific anatomical features on a patient's body during a medical procedure. For example, a user may wish to identify an anatomical region and/or body part of the patient's body in an image of the body which is provided to the user by displaying the information contained in data acquired by using an imaging method. The term of user in this context encompasses medical personnel such as physicians and their assistants as well as technically skilled personnel such as medical physicists. For example, the user may wish to locate an anatomical region which he is able to view on the patient in an image which comprises image information about the anatomical region. To this end, he will preferably use the pointer to point at the anatomical region and localize the pointer relative to the position of the anatomical region such that by guidance via the navigation system, he will be provided with information about the location of representation of the anatomical region in the image. This information may be provided, for example, by way of colour highlighting or other means of graphical emphasis in the image.

As mentioned, the image of the anatomical region is acquired by using an imaging method. In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), X-ray tomography, magnetic resonance tomography (MRT or MRI), conventional X-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure.

In order to identify the representation of the anatomical region in the image information, at least part of the patient's body (in particular, the anatomical region) is preferably registered with the image information about the patient's body or the anatomical region, respectively. Registering in particular encompasses transforming information about the position of the anatomical region into a common coordinate system in which coordinates of real parts of the patient's body and of the corresponding parts in the image are described. The n-dimensional image of a body is registered when the spatial location of each point of an actual object within a space, for example a body part in an operating theatre, is assigned an image data point of an image (CT, MR, etc.) stored in a navigation system. Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

In order to acquire a position of the medical device, in particular a pointer, relative to the anatomical region, the relative position of the medical device may be acquired directly by a navigation system by means of a main detection device which detects the position of the medical device and preferably also of the anatomical body, for example by optical detection employing passive or active markers (attached for instance to the medical device and for instance to the anatomical body). For determining the position of the medical device relative to the anatomical region, information about a position of the medical device relative to a reference structure is preferably acquired, in particular by using a supplement detection device. The supplement detection device can be in particular positioned independent from (and in particular moved relative to) the main detection device and is in particular separate from the main detection device. The supplement detection device can be configured to detect both the position of the medical device and the position of the reference structure or to have a fixed and predetermined (known) relative position to one of the medical device and the reference structure and to detect the position of the other one of the medical device and the reference structure.

Within the framework of the invention, it is preferred that main position data (also called reference structure position data) comprising reference structure position information is acquired. The reference structure position information describes the position of a reference structure in a global coordinate system. The reference structure preferably is a physical structure, for example an apparatus or part of a room such as a wall. However, it is also envisaged to use a predefined spatial arrangement of a plurality of physical structures as a reference structure. The reference structure preferably rests in the global coordinate system. In case the reference structure is a tracked physical structure, the global coordinate system in which its position is described (in particular, the global coordinate system) may be denoted "tracking coordinate system". A tracked physical structure is in particular tracked or configured to be tracked by a navigation system. Tracking encompasses acquiring information about a position of the tracked physical structure. Such a position information acquisition preferably is conducted continuously or at least for a multitude of discrete, consecutive points in time and preferably also space. However, tracking also encompasses acquisition of the position information also for only a single point in space and/or time. The entity may be tracked by, for example, attaching a retroreflective marker to it in a predetermined, preferably fixed spatial relationship and detecting the marker by means of a navigation system on the basis of optical detection. The reference structure preferably serves as a structure relative to the position of which the medical device is localized. According to a preferred embodiment of the invention, the reference structure comprises a marker device and in particular is a marker device.

Preferably, supplement position data (which may also be called relative position data) is acquired which comprises relative position information. The relative position data is in particular received from the supplement detection device. The relative position information in particular describes a position of the medical device relative to the position of the reference structure. The position of the medical device relative to the position of the reference structure is preferably described by coordinates in a reference coordinate system which in a preferred embodiment of the invention rests relative to the position of the medical device but can also be a reference coordinate system in which the reference structure rests or any other coordinate system. However, the medical device preferably is movable, in particular movable relative to the global coordinate system in which the position of the reference structure is defined. More particularly, the medical device is movable relative to the reference structure. The global coordinate system and the reference coordinate system may be identical or, preferably, different from one another. In particular, their origins may differ. In this latter case, in particular a transformation between the two coordinate systems is not equal to the identity transformation (also called unity). Preferably, the reference coordinate system moves relative to the global coordinate system (in particular, the origins of the two coordinate systems move relative to one another).

Preferably, acquiring the supplement position data includes detecting the reference structure, in particular the position of the reference structure, from a perspective of the medical device. According to a preferred embodiment, a supplement detection device for detecting the position of the reference structure (hereinforth also called reference detection means), in particular for detecting the reference structure itself, is placed relative to the reference structure so that it has a preferably unobstructed view of the reference structure. Preferably, the supplement detection device detects the position of the reference structure by optical means. That is, the reference detection means acquires image data. Therefore, the reference detection means is preferably embodied by a data acquisition unit which has a fixed position relative to the medical device and which is in particular comprised by the medical device. Therefore, the position of the reference structure can also be described as being detected by means of the medical device. The supplement detection device can also be positioned separately from the medical device and the reference structure to detect both the medical device and the reference structure and thus the relative position between the reference structure and the medical device. The supplement detection device can also be part of the reference structure, i.e. can have a fixed spatial relationship to the reference structure. The prior art uses just one main detection device which detects (or, more specifically, has to detect) both the medical device and the anatomical structure. However, if there is an obstacle like the reference structure, then detection of the medical device by the main detection device can be impossible. The supplement detection device detects (or, more specifically, has to detect) just the relative position between the medical device and the reference structure (e.g. the obstacle) in order to provide sufficient supplementary information for determining the position of the medical device. This results in new options for positioning the supplement detection device compared to the use of only a main detection devices. This allows for navigation even in areas totally obscured by the reference structure. According to one embodiment, the supplement detection device comprises an imaging device such as a camera (in particular, a digital camera which is configured to take photographs and/or record video sequences). According to another embodiment, the supplement detection device comprises an antenna device which is configured to support direction finding of a corresponding transceiver device associated with the reference structure, such as an oscillating circuit. Preferably, the supplement detection device detects a detectable means for defining the position of the reference structure (hereinforth called reference definition means). The reference definition means comprises detectable features like the geometry (shape and/or size) of the reference definition means and/or a detectable pattern, like a pattern detectable by electromagnetic radiation (e.g. an electric circuit pattern like an RFID or an optically detectable pattern like a graphic pattern). The reference definition means and in particular the feature are detectable by preferably both the main detection device and the supplement detection device. The main detection device can be constituted to detect the same or different features than the supplement detection device. The reference detection means is in particular a marker device having a predetermined (in particular, fixed) spatial relationship relative to the reference structure. The reference structure preferably comprises the reference definition means.

Where in this disclosure reference is made to determining a position (in particular, of a specific entity) relative to the reference structure and/or relative to the position of the reference structure, such disclosure may be equally understood to mean determining the position (in particular, of the same entity) relative to the reference definition means and/or relative to the position of the reference definition means and vice versa. Furthermore, determining the (absolute) position of the reference structure (in particular, in the global coordinate system) is equivalent in meaning to determining the (absolute) position of the reference definition means (in particular, in the global coordinate system).

If the supplement detection device is, for example, a camera, the reference definition means preferably is a graphical image pattern which has a predetermined (in particular, fixed) spatial relationship relative to the reference structure. For example, a graphical pattern may be painted, written or engraved on a surface of the reference structure. Alternatively or additionally, a label with markings embodying the graphical pattern may be attached to a surface of the reference structure. According to a very preferred embodiment, the outer appearance of the reference structure is used as a reference definition means. The outer appearance of the reference structure is in particular defined by its physical appearance and/or geometry. Where in this disclosure reference is made to an appearance of the reference structure, such disclosure is equally applicable to an appearance of the reference definition means. According to a very preferred embodiment, the outer appearance is defined by specific geometric and/or visually recognizable features which are in particular unique for the reference structure or type of reference structure used. Such features are in this disclosure also called appearance features. In particular, the appearance features can be defined by image information. In other words, the outer appearance can also be described as an image appearance, in particular an image appearance in two dimensions. The appearance features may be defined by geometric features such as angles and/or distances and/or graphical features such as colour contrasts between different image features and/or colour shades and/or shapes and/or dimensions (in particular two-dimensional shapes or dimensions) of image features.

Preferably, the supplement detection device acquires image data comprising image information about the outer appearance of the reference structure, in particular the reference definition means (in this case, also called image appearance). The image data preferably is digital data and comprises image information which is divided into discrete portions such as pixels or voxels. The image information may be acquired as information about a moving image (i.e. video image information) or as information about a stationary picture (e.g. a photograph, in particular digital photograph). The image information may be multicolour information or greyshade information.

Preferably, reference structure appearance data is acquired which comprises basic appearance information. The basic appearance information is preferably predetermined image information and in particular describes a basic image appearance of the reference structure, in particular the reference definition means, in particular of its appearance features. The basic image appearance is in particular defined by appearance features as described above regarding the outer appearance. The reference structure appearance data is preferably predetermined and provided to the inventive method. The reference structure appearance data further preferably comprises information about appearance features of the reference definition means. The appearance information is then preferably compared to the image information acquired by the data acquisition unit. In particular, the step of comparing comprises determination of appearance features in the image information and comparing them to the appearance features described by the appearance information. The appearance features may be determined from the image information for example by edge detection. Alternatively or additionally, corresponding points in two stereoscopic images taken by the data acquisition unit may be compared to corresponding points defined by the appearance information. In this case, the data acquisition unit preferably comprises a stereoscopic camera.

Preferably, perspective data is determined which comprises actual perspective information about an actual perspective of the medical device towards the reference definition means. The actual perspective of the medical device is in particular defined by a geometric projection, for example a projection from the position of the supplement detection device (which is for instance comprised by the medical device) towards the position of the reference structure (for instance towards the reference definition means). Preferably, this projection is defined in the reference coordinate system. The actual perspective information is preferably determined by comparing the basic appearance information (in particular information on the geometry of the reference structure) to the image information, in particular by determining a difference in perspective, in particular a perspective distortion of the image appearance of the reference definition means compared to a basic perspective upon which the basic image appearance defined by the basic appearance information is based. Perspective distortion is a warping or transformation of an object, the object being in particular an image object described by image information, that differs significantly from what the object would look like when viewed at a normal focal length, the distortion being in particular due to the relative scale of nearby and distant features located in the (imaged) surrounding area of the object. Perspective distortion is determined by the relative distances at which the image contained in the image information is captured and viewed, and is due to the angle of view of the image (as captured) being either wider or narrower than the angle of view at which the image is viewed, hence the apparent relative distances differing from what is expected. In short, perspective distortion is influenced by the relationship between two factors: the angle of view at which the image is captured by an imaging device such as a camera and the angle of view at which the image of the object is presented or viewed. Perspective distortion takes two forms: extension distortion and compression distortion, also called wide-angle distortion and long-lens or telephoto distortion, when talking about images with the same field size. Extension of wide-angle distortion can be seen in images shot from close using a wide-angle lens (with an angle of view wider than a normal lens). Objects close to the lens appear abnormally large relative to more distant objects, and distant objects appear abnormally small and hence more distant—distances are extended. Compression, long-lens or telephoto distortion can be seen in images shot from a distance using a long focus lens or the common telephoto sub-type (with an angle of view narrower than a normal lens). Distant objects look approximately the same size—closer objects are abnormally small, and more distant objects are abnormally large, and hence the viewer cannot discern relative distances between distant objects—distances are compressed. Note that perspective distortion is caused by distance, not by the lens per se. Two shots of the same scene from the same distance will exhibit identical perspective distortion, regardless of lens used. The basic perspective is in particular defined by a predetermined projection in analogy to the definition of the actual perspective, for example, a normal projection or central perspective of the reference structure. The basic perspective is more particularly defined for a particular angle of view at a particular distance from the reference structure (which preferably is equal to the normal focal length of an optical system which is preferably used by the supplement detection device for detecting the reference structure). By way of image analysis, a deviation of the actual perspective from the basic perspective can be determined. Determining the angle of view and distance from the reference structure is preferably supported by using a stereoscopic camera as the supplement detection device for gathering the perspective data. Preferably, the same device or a device having equivalent optical characteristics is used for gathering the reference structure appearance data. Preferably the difference in perspective is determined by comparing the location of appearance features in the actual perspective information to their location in the basic appearance information.

Based on the perspective information, the relative position information can thus be determined. In particular, the position of the medical device relative to the position of the reference structure is determined by inverting the actual perspective (or the projection underlying the actual perspective, respectively) so that the relevant, in particular linear, equations can be solved for the relative position of the data acquisition unit and/or the medical device.

Preferably, the reference structure appearance data is stored in a database. Alternatively or additionally, the database may comprise reference structure geometry data comprising reference structure geometry data. The reference structure geometry data preferably comprises information about the geometry (shape and/or size) of a plurality of potential reference structures. The reference structure geometry information may be used to determine the actual perspective based on a comparison of the reference structure geometry information with the actual perspective information. In particular, the basic perspective information may be acquired based on the reference structure geometry information.

Based on the relative position information and the reference structure position information, the position of the medical device in the global coordinate system can be determined. The position of the medical device in the global coordinate system preferably is described by medical device position information contained in medical device position data. The medical device position data is thus preferably determined based on the relative position data (in particular, based on the relative position information) and the reference structure position data (in particular, based on the reference structure position information).

From the above description, it becomes clear that, in contrast to prior art approaches, the medical device is actively tracked, in particular (actively) tracks itself. That is, the medical device is configured to determine data by itself, which data is used for extracting information which describes the position of the medical device. In prior art approaches, the medical device is passively tracked since the medical devices disclosed in those approaches are not configured to determine and/or collect data by themselves. In order to implement the inventive method, the medical device is preferably provided with or at least associated with (i.e. connected to) a supplement detection device which is used for detecting the relative position data. In prior art approaches, such a detection device (if present at all) will be located externally from the medical device and will not be in a predetermined (in particular fixed) spatial relationship with the medical device, whereas according to this invention the medical device is preferably internally provided with the supplement detection device in preferably a predetermined (in particular fixed) spatial relationship. According to the invention, the medical device may thus be described as being self-localizing.

Preferably, the reference structure position data and the relative position data are acquired by using different tracking modalities. The term of tracking modality encompasses the data acquisition method which is used for the tracking. For example, one tracking modality may be localization by imaging of radioopaque markers by X-rays and another tracking modality may be localization by use of retroreflective markers. A further tracking modality is embodied by the above-described method of image-based tracking which is in particular based on analyzing image information and preferably determining a perspective described by the image information.

The reference position data is acquired preferably by using a main tracking modality (also called primary tracking modality). The primary tracking modality is in particular used to determine the position of the reference structure in the global coordinate system. According to a specific embodiment of the invention, the reference structure position data and the relative position data are acquired by using the same tracking modality. In this case, acquiring the relative position data includes detecting the position of the reference structure from a perspective of the medical device preferably only if tracking the medical device by using the primary tracking modality is hampered. For example, a line of sight from a tracking device to the medical device may be hampered (which may be determined as the medical device not being detectable for the primary tracking modality), for example by placing an obstacle in the line of sight. The obstacle in particular is not transparent for the electromagnetic radiation used by the specific tracking modality. In that case, for example, no response is received by the tracking device from the medical device which would indicate the position of the medical device. Then, a system, in particular navigation system, used for implementing the inventive method may switch to localizing the medical device by using a supplement tracking modality (also called secondary tracking modality) which preferably includes the above-described tracking based on image analysis. The secondary tracking modality is preferably used to only track the medical device. In this case, the first and second tracking modalities preferably are different modalities. In particular, the secondary tracking modality is not used for tracking the reference structure.

According to a further embodiment of the invention, the secondary tracking modality may be continuously activated (i.e. activated throughout execution of at least all of the inventive method) and localize the medical device even if there does not exist the above-described line of sight problem. In this case, the medical device is localized preferably only using the secondary tracking modality. The primary tracking modality then is preferably used to track only the reference structure.

According to still a further embodiment, the reference structure may not be tracked. The reference structure reference position data then is preferably provided to the inventive method as predetermined data, comprising information about the position of the reference structure, in particular described in the global coordinate system. This may be particularly useful if the reference structure is not movable or not moved, in particular not movable and/or not moved relative to the patient's body and/or the anatomical region.

Preferably, the position of the medical device is determined relative to the reference structure and/or the patient's body, in particular an anatomical region of interest. A position of the medical device in the global coordinate system, is determined by combining measurements of the position of a reference structure in the global coordinate system and the measurement of the position of the reference structure in a reference coordinate system which in particular rests relative to the medical device. The latter measurement is preferably carried out by activating the reference definition means of the medical device. This combination preferably relies on processing the position measurements in series (i.e. using the position of the medical device relative to the reference structure as an input for computing its position in the global coordinate system), whereas prior art techniques rely on a direct measurement of the position of the medical device in the global coordinate system, in particular a simultaneous direct measurement (also called a measurement in parallel, in particular by using the primary tracking modality for localizing both the reference structure and the medical device). Specific advantages of processing the position measurements in series (which may also be called serial localization) are that measurement errors for each of the steps of position determination in the global coordinate system and reference coordinate system typically have to be added and may therefore be determined each by themselves. Furthermore, the measurement errors may be notified to a user taken by themselves for as a sum. Information about the measurement errors may be contained in corresponding position determination error data as position determination error information. The position determination error information in particular comprises information about the error associated with determining the reference structure position information and/or the relative position information.

Preferably, the method also includes determining whether the position of the medical device can be determined based on the main position data. In particular if such a determination is possible, user information data comprising information which describes the position of the medical device may be output. Preferably, the user information data is based on the supplement position data if the position of the medical device cannot be determined based on the main position data or if a determination based on the position data would have an accuracy below a predetermined value or if the accuracy of the determination based on the main position data is below the accuracy of the determination based on the relative position information and the reference structure position information as described above.

In particular, the inventive method includes transforming a position of the medical device in the reference coordinate system into a position of the medical device in the global coordinate system. As mentioned above, the present invention provides the advantage of supporting localization of a medical device in case of failure of a primary tracking modality. This advantage is achieved at least partly by the fact that the medical device does not need to be tracked or trackable by the tracking system used for tracking the reference structure but can autonomously localize itself in relation to the reference structure and/or the position of the reference structure.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

The invention also relates to a navigation system for computer-assisted medical procedures (in particular surgery), comprising the computer on which the aforementioned program is running, for processing the acquired data;

the main and supplement detection device for detecting signals describing the positions to be determined in the method and for supplying digital data corresponding to the signals to the computer via a data interface (for example, an analog digital converter); and preferably a user interface for receiving data from the computer in order to provide information to the user, wherein the received data are generated by the computer on the basis of the results of the processing performed by the computer.

The navigation system is preferably embodied by a system for acquiring (in particular, determining) the position of the medical device to be localized which is in particular configured to execute the above-described method. This system preferably comprises the reference structure and the medical device. Furthermore, the system preferably comprises a reference structure position acquisition unit which is configured to acquire the reference structure position data and serves as the mentioned main detection device. The system preferably also comprises a device localizing unit which is configured to acquire, by detecting the position of the reference structure (in particular, by detecting the reference definition means) from a perspective of the medical device, the relative position information data. The device localizing unit serves as the mentioned supplement detection device. The system preferably further comprises a computer which is operatively coupled to the reference structure position acquisition unit and the device localizing unit and which is configured to determine, based on the reference structure position information and the relative position information, the medical device position data.

The reference structure position acquisition unit preferably is a tracking system (or at least part of such a tracking system), in particular a tracking system which operates based on an optical tracking modality. The term of optical tracking modality encompasses in particular tracking modalities which employ reflections of electromagnetic radiation which has been emitted in the sub-X-ray wavelength range (in particular, in the infrared wavelength range or in the visible wavelength range) for tracking the reference structures (or, more particularly, reflective markers) or which employ such radiation emitted by active markers and received by the tracking system. Alternatively or additionally, the reference structure position acquisition unit may be a non-volatile digital storage unit (e.g., a hard disc or flash memory) in which the reference structure position data is stored. More generally, the reference structure position acquisition unit may be a computer operatively coupled to such a digital storage unit.

The device localizing unit preferably is comprised by, in particular a part of the medical device. Alternatively or additionally, the device localizing unit may be a tracking system which is configured to track the medical device. According to a very preferred embodiment, the device localizing unit is the aforementioned data acquisition unit which is in particular configured to detect the reference structure. More particularly, the device localizing unit is embodied by an imaging device such as a camera.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

Preferably, the inventive method is at least partly executed by a computer. That is, all steps or just some of the steps (i.e. less than a total number of steps) of the inventive method may be executed by a computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Figure 2:
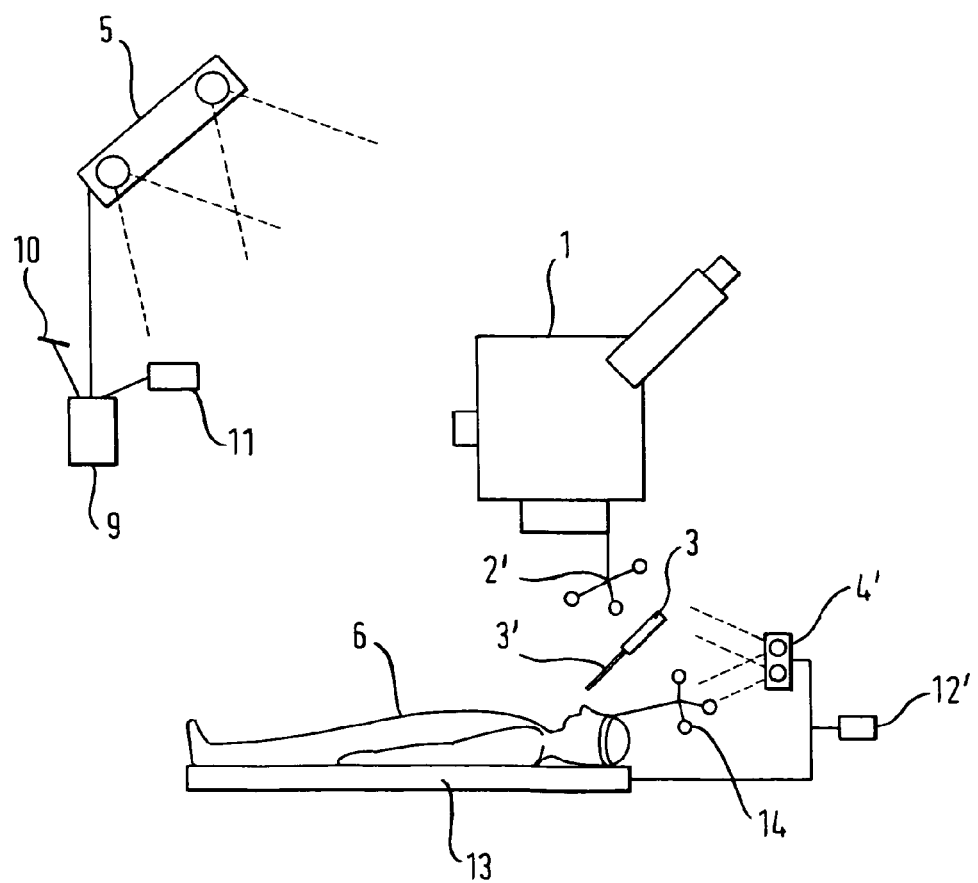

In the following, a preferred embodiment of the invention which shall not be construed as limiting the scope of the invention is described with reference to the figures, wherein FIG. 1 shows an embodiment of the system for acquiring the position of the medical device with a camera which is internal to the medical device; and FIG. 2 shows an embodiment of the system for acquiring the position of the medical device with a camera which is external to the medical device.

As shown by FIG. 1, a pointer 3 is used to identify the position of a part of a patient's body 6. In this example, a microscope 1 is used to view that part of the patient's body. The microscope 1 serves as a reference structure and is tracked by a stereoscopic camera 5 (serving as a reference structure position acquisition unit) which acquires the position of the reference star 2 (serving as a reference definition means) which has a predetermined and fixed spatial relationship to the microscope 1. The position of the patient's body 6 and/or its individual parts in the coordinate system of the stereoscopic camera 5 which serves as the global coordinate system is preferably determined by referencing it with the global coordinate system by for example imaging it with a medical imaging method. In particular, the analytical device which is used for the medical imaging has a predetermined position in the global coordinate system such that the position of the patient's body 6 and/or its individual parts in the global coordinate system may be determined from analysis of the image information about the patient's body 6 and/or its individual parts generated by using the analytical device. As will become clear, the position of the pointer 3 relative to the patient's body 6 and/or its individual parts may therefore be determined.

Where in the description of the figures a position of the pointer 3 is determined, such description may be equally applied to determining the position of the pointer tip 3' due to the preferably predetermined position of the pointer tip 3' relative to the other constituents of the pointer 3 (such as its handle).

In the arrangement of FIG. 1, the pointer 3 cannot be tracked by the stereoscopic camera 5 since the microscope 1 blocks the line of sight between the stereoscopic camera 5 and the pointer 3. In particular, the microscope 1 is an obstacle in the line of sight between the stereoscopic camera 5 and the pointer 1, more particularly an obstacle which is not transparent for the electromagnetic radiation used for tracking the microscope 1 and/or reference star 2. The pointer 3 serves as the medical device in the sense of the invention and preferably has a predetermined and fixed spatial relationship to the device camera 4 serving as the data acquisition unit and/or device localizing unit. In particular, the device camera 4 is moved along the same trajectory along with the pointer 3 is moved during a medical procedure. However, the position of the microscope 1 in a global coordinate system may be determined by acquiring the reference structure position data by using the stereoscopic camera 5 if the microscope 1 is used as the reference structure. The global coordinate system may be defined as resting relative to the position of the stereoscopic camera 5. The stereoscopic camera 5 in this case serves as the reference structure position acquisition unit.

The device camera 4 has a field of view 7 of preferably conical shape. The device camera 4 acquires image data of the surface of the microscope 1, in particular the surface or surface regions of the microscope 1 which point towards the patient's body 6. Specific image features serving as appearance features 8 such as corner edges and/or other shapes defined by the surface (in particular, the surface geometry) of the microscope 1 are imaged by the device camera 4 and used to acquire the position of the device camera 4 and the pointer 3 relative to the microscope 1.

Pointer 3 preferably comprises a data transmission unit 12 for transmitting the image data acquired by the device camera 4 to the computer 9, which in particular is the aforementioned computer of the system for acquiring the position. The computer 9 is connected to the stereoscopic camera 5 via a data transfer connection and to a monitor 11 for graphical display of information. The data transmission unit 12 is a wireless transmission device which transmits electromagnetic signals which are received by the data reception unit 10 connected to the computer 9. The data reception unit 10 preferably comprises an antenna. The computer 9 is preferably provided with the aforementioned reference structure appearance data, wherein the appearance information stored in that data comprises information about the appearance features 8. The image data is then compared by the computer to the reference structure appearance data in order to determine the perspective data which comprises the aforementioned perspective information. To this end, the relative positions between a plurality of appearance features 8 as described by the image information (contained in the image data) may be compared to the relative positions of the same plurality of appearance 8 as defined by the appearance information. The result of this comparison may for example be that the relative positions between the device camera 4 and/or pointer 3 and the microscope 1 differ between those described by the image information and those described by the basic appearance information. This difference is then used to determine a projection from the position of the pointer 3 or the device camera 4, respectively to the position of the microscope 1. Since the position of the microscope 1 in the global coordinate system and the relative position between at least the device camera 4 and/or the pointer 5 and the microscope 1 are known, this projection may be used to determine the position of the pointer 3 in the global coordinate system. Thereby, it is possible to acquire the position of a part of the patient's body 6 in the global coordinate system at which the device camera 4 and/or the pointer 3 are if the body part is pointed at with the pointer 3. In particular, the spatial relationship between the device camera 4 and the pointer tip 3' is known such that the pointer tip 3' may be used to determine the position of the body part.

Alternatively or additionally, the position of a part of the patient's body 6 in the global coordinate system may be predetermined and known. The device camera 4 may then be used to image this body part and to evaluate specific geometric features of that body part in order to determine a perspective from the pointer 3 to that body part. The image data thus taken may then be correlated to known patient image data which may have been acquired by using a medical imaging modality (and stored as basic appearance information). In this way, the position of the pointer 3 in the global coordinate system may be determined in analogy to the aforementioned method.

As becomes clear from the above description, the pointer 3 is configured to autonomously localize itself in relation to an object localized by a first tracking system such as the stereoscopic camera 5. The device camera 4 (which may be a video camera or a plurality of cameras) is used to take image data of a reference structure and to correlate this preferably three-dimensional image information with a model of the reference structure to determine the position of the medical device in relation to that model and therefore in relation to the reference structure.

If the device localizing unit is a camera, in particular a video camera, for example a prism and/or a mirror (a simple, multi-surface or convex mirror) can be used to split the field of view 7 into multiple parts to widen the field of view and/or to add multiple perspectives which may in particular be evaluated simultaneously in order to reduce errors in acquiring the relative position information.

According to FIG. 2, a patient's body 6 is placed on a bed 13 which is connected with a stereoscopic supplement detection camera 4' in preferably a predetermined spatial relationship between the supplement detection camera 4' and the bed 13. The supplement detection camera 4' is located external from the pointer 3 and is placed such it is able to detect, in particular image, a reference star 2' attached to the microscope 1 in a predetermined spatial relationship and the pointer 3 and optionally a reference star 14 attached to the patient's body 6 in a predetermined relationship. Preferably, the position of the reference stars 2' and 14 in the global coordinate system is acquired from data gathered by stereoscopic camera 5. Supplement detection camera 4' is also connected to wireless transmission unit 12' which is configured to transmit the image data gathered by the supplement detection camera 4' to the data reception unit 10 which is operatively coupled to the computer 9. The computer 9 is as before also operatively coupled to the monitor 11.

According to FIG. 2, the position of the pointer 3 in the global coordinate system may be determined by image analysis such an image analysis preferably determines the position of the pointer 3 relative to the reference star 14 and/or the reference star 2'. Since the position of the reference stars 2', 14 in the global coordinate system is known from the position of the pointer 3 in the global coordinate may be determined based on the relative position between the pointer 3 and the reference star 2' and/or the reference star 14.

The embodiment of FIG. 2 may also be adapted to the embodiment of FIG. 1. For example, the position of the patient's body 6 in the arrangement of FIG. 2 may be predetermined by analysis of medical images as described with reference to FIG. 1 and the position of the pointer 3 with regard to the patient's body 6 and/or its individual parts may then be determined from the relative position of the pointer 3 relative to the patient's body 6 and/or its individual parts based on image information gathered by the supplement detection camera 4'. In analogy, the position of the patient's body 6 and/or its individual parts in the embodiment of FIG. 1 may be determined by attaching a reference star 14 to the patient's body 6 as described with reference to FIG. 2. The position of the pointer 3 relative to the patient's body 6 and/or its individual part may then be determined based on image information of the pointer 3 and the patient's body 6 and/or its individual parts gathered by the device camera 4. Based on the information about this relative position, the position of the pointer 3 in the global coordinate system may thus be determined.

A specific advantage of the embodiment of FIG. 2 compared to the embodiment of FIG. 1 is that the field of view of supplement detection camera 4' is not dependent on the orientation of the pointer 3.

In particular in case the camera 5 (main detection device) can detect the position of the reference star 14 (but not the position of the pointer, i.e. of the medical device), then the reference star 14 can be used as the reference structure in order to determine the position of the pointer (medical device) by means of the camera 4' (supplement detection device), if the camera 4' detects both the reference star 14 and the pointer.

The invention claimed is:

1. A method of tracking a position of a medical device in a system comprising the medical device, a first detection device, a second detection device that is continuously maintained in a fixed spatial relationship relative to the medical device, a reference structure, a display, and a computer operatively associated with the first detection device, the second detection device, and the display, the method comprising:
    a) determining by the computer using the first detection device a global position of the reference structure in a global coordinate system;
    b) determining, by the computer using the second detection device that is continuously maintained in a fixed spatial relationship relative to the medical device, a relative position of the medical device relative to the reference structure in a reference coordinate system;
    c) determining, by the computer, a tracked position of the medical device in the global coordinate system based on the global position of the reference structure and the relative position of the medical device;
    d) determining, by the computer, user information data based on the tracked position of the medical device; and
    e) displaying the user information data on the display.

2. The method according to claim 1, wherein the second detection device is attached in a fixed spatial relationship to the medical device.

3. The method according to claim 1, wherein the reference structure includes a reference definition means for defining the position of the reference structure, the reference definition means having detectable geometry features and/or a detectable graphic pattern.

4. The method according to claim 3, wherein the determining the global position of the medical device comprises:
    determining, by the computer using the first detection device, a position of the reference definition means in the global coordinate system; and
    determining, by the computer, the global position of the reference structure based on the position of the reference definition means.

5. The method according to claim 3, wherein:
    the determining the relative position of the medical device relative to the reference structure includes detecting the reference definition means by the second detection device that is continuously maintained in a fixed spatial relationship relative to the medical device.

6. The method according to claim 5, comprising:
    acquiring, by the computer, reference appearance information that describes a reference image appearance of the reference definition means;
    determining, using the second detection device that is continuously maintained in a fixed spatial relationship relative to the medical device, actual reference appearance information that describes an actual image appearance of the reference definition means;
    determining, by the computer, actual perspective distortion information based on a comparison of the reference appearance information and the actual reference appearance information; and
    determining the relative position of the medical device relative to the reference structure based on the actual perspective distortion information.

7. The method of claim 6, wherein the determining the actual perspective distortion information includes:
    defining, by the computer using the reference appearance information, a basic perspective based on a particular angle of view at a particular distance from the reference definition means;
    determining, by the computer, an actual perspective based on the actual reference appearance information,
    determining, by the computer, the actual perspective distortion information based on the basic perspective and the actual perspective.

8. The method of claim 3, wherein the reference definition means is defined by the physical appearance and/or geometry of the reference structure.

9. The method according to claim 1, comprising:
    acquiring, by the computer, reference appearance information that describes a reference image appearance of the reference structure and;
    determining, using the second detection device that is continuously maintained in a fixed spatial relationship relative to the medical device, actual reference appearance information that describes an actual image appearance of the reference structure;
    determining, by the computer, actual perspective distortion information based on a comparison of the reference appearance information and the actual reference appearance information; and
    determining the relative position of the medical device relative to the reference structure based on the actual perspective distortion information.

10. The method of claim 9, wherein the determining the actual perspective distortion information includes:
    defining, by the computer using the reference appearance information, a basic perspective based on a particular angle of view at a particular distance from the reference structure;
    determining, by the computer, an actual perspective based on the actual reference appearance information; and
    determining, by the computer, the actual perspective distortion information based on the basic perspective and the actual perspective.

11. The method of claim 1, wherein the reference structure is medical equipment to be used in a medical procedure.

12. A non-transitory computer readable storage medium storing a computer program for tracking a position of a medical device in a system comprising the medical device, a first detection device, a second detection device that is continuously maintained in a fixed spatial relationship relative to the medical device, a reference structure, a display, and a computer comprising the non-transitory computer readable storage medium that is operatively associated with the first detection device, the second detection device, and the display, which, when running on a computer or when loaded onto a computer, causes the computer to:
- a) determine, using the first detection device, a global position of the reference structure in a global coordinate system;
- b) determine, using the second detection device that is continuously maintained in a fixed spatial relationship relative to the medical device, a relative position of the medical device relative to the reference structure in a reference coordinate system;
- c) determine a tracked position of the medical device in the global coordinate system based on the global position of the reference structure and the relative position of the medical device;
- d) determine user information data based on the tracked position of the medical device; and
- e) display the user information data on the display.

13. A system for tracking a position of a medical device, comprising:
- the medical device;
- a first detection device;
- a second detection device that is continuously maintained in a fixed spatial relationship relative to the medical device;
- a reference structure;
- a display; and
- a computer operatively associated with the first detection device, the second detection device, and the display, the computer configured to:
  - a) determine, using the first detection device, a global position of the reference structure in a global coordinate system;
  - b) determine, using the second detection device that is continuously maintained in a fixed spatial relationship relative to the medical device, a relative position of the medical device relative to the reference structure in a reference coordinate system;
  - c) determine a tracked position of the medical device in the global coordinate system based on the global position of the reference structure and the relative position of the medical device;
  - d) determine user information data based on the tracked position of the medical device; and
  - e) display the user information data on the display.

14. The system according to claim 13, wherein the second detection device is attached in a fixed spatial relationship to the medical device.

* * * * *